(12) United States Patent
Chilinski et al.

(10) Patent No.: US 8,402,670 B2
(45) Date of Patent: Mar. 26, 2013

(54) TENSILE BAR MARKING FIXTURE

(75) Inventors: Daniel Chilinski, Livonia, MI (US); Josephine A. Hlavna, Commerce Township, MI (US); Brian M. Deames, Ann Arbor, MI (US)

(73) Assignee: Toyota Motor Engineering & Manufacturing North America, Inc., Erlanger, KY (US)

( * ) Notice: Subject to any disclaimer, the term of this patent is extended or adjusted under 35 U.S.C. 154(b) by 285 days.

(21) Appl. No.: 12/774,774

(22) Filed: May 6, 2010

(65) Prior Publication Data

US 2011/0271766 A1 Nov. 10, 2011

(51) Int. Cl.
*B43L 13/24* (2006.01)
*B25D 5/00* (2006.01)

(52) U.S. Cl. .................. 33/577; 33/578; 33/19.1

(58) Field of Classification Search .......... 33/32.1–32.7, 33/41.1–45, 706, 712, 790, 791, 501.45, 33/577, 578, 19.1
See application file for complete search history.

(56) References Cited

U.S. PATENT DOCUMENTS

| | | | | |
|---|---|---|---|---|
| 2,786,278 A * | 3/1957 | Bates | | 33/662 |
| 2,849,803 A * | 9/1958 | Wade | | 33/577 |
| 3,310,979 A * | 3/1967 | Hall | | 73/844 |
| 3,645,000 A * | 2/1972 | Gass | | 33/759 |
| 3,803,907 A | 4/1974 | Ryckman et al. | | |
| 3,885,424 A | 5/1975 | Ryckman et al. | | |
| 3,916,681 A | 11/1975 | Ryckman et al. | | |
| 3,955,446 A | 5/1976 | Mundy | | |
| 3,975,950 A | 8/1976 | Erdei | | |
| 4,031,746 A * | 6/1977 | Furuta et al. | | 73/800 |
| 4,112,746 A * | 9/1978 | Itoh et al. | | 73/789 |
| 4,499,666 A * | 2/1985 | Smith | | 33/562 |
| 4,571,802 A | 2/1986 | Calhoun et al. | | |
| 4,670,990 A * | 6/1987 | Horvath | | 33/562 |
| 4,841,779 A * | 6/1989 | Mitsuhashi et al. | | 73/826 |
| 5,193,398 A * | 3/1993 | Harder et al. | | 73/834 |
| 5,396,710 A * | 3/1995 | Battaglia | | 33/429 |
| 6,094,259 A * | 7/2000 | Kamegawa | | 356/32 |
| 6,272,758 B1 * | 8/2001 | Wheeler | | 33/1 G |

* cited by examiner

*Primary Examiner* — Lisa Caputo
*Assistant Examiner* — Jonathan Dunlap
(74) *Attorney, Agent, or Firm* — Gifford, Krass, Sprinkle, Anderson & Citkowski, P.C.

(57) ABSTRACT

The present invention provides an apparatus and method to accurately scribe benchmarks into a tensile test sample bar. The apparatus includes a base having a planar surface allowing a tensile test sample bar to rest thereupon. The apparatus further includes a guide having two spaced apart edges separated by a predetermined width. The planar surface of the base further includes a plurality of grid lines to properly align the tensile test sample bar. The base further includes at least one securing member adapted to abut and secure the guide during scribing of the tensile test sample bar. The method includes the steps of aligning a tensile test sample bar on the planar surface having a plurality of grid lines and securing the tensile test sample bar on the planar surface by means of the securing members. The guide then provides for an accurate predetermined width of the spacing of the benchmarks scribed onto the tensile test sample bar. By means of a scribe, the user runs the scribe along each of the edges of the guide and scrapes two benchmarks onto the tensile test sample bar.

14 Claims, 3 Drawing Sheets

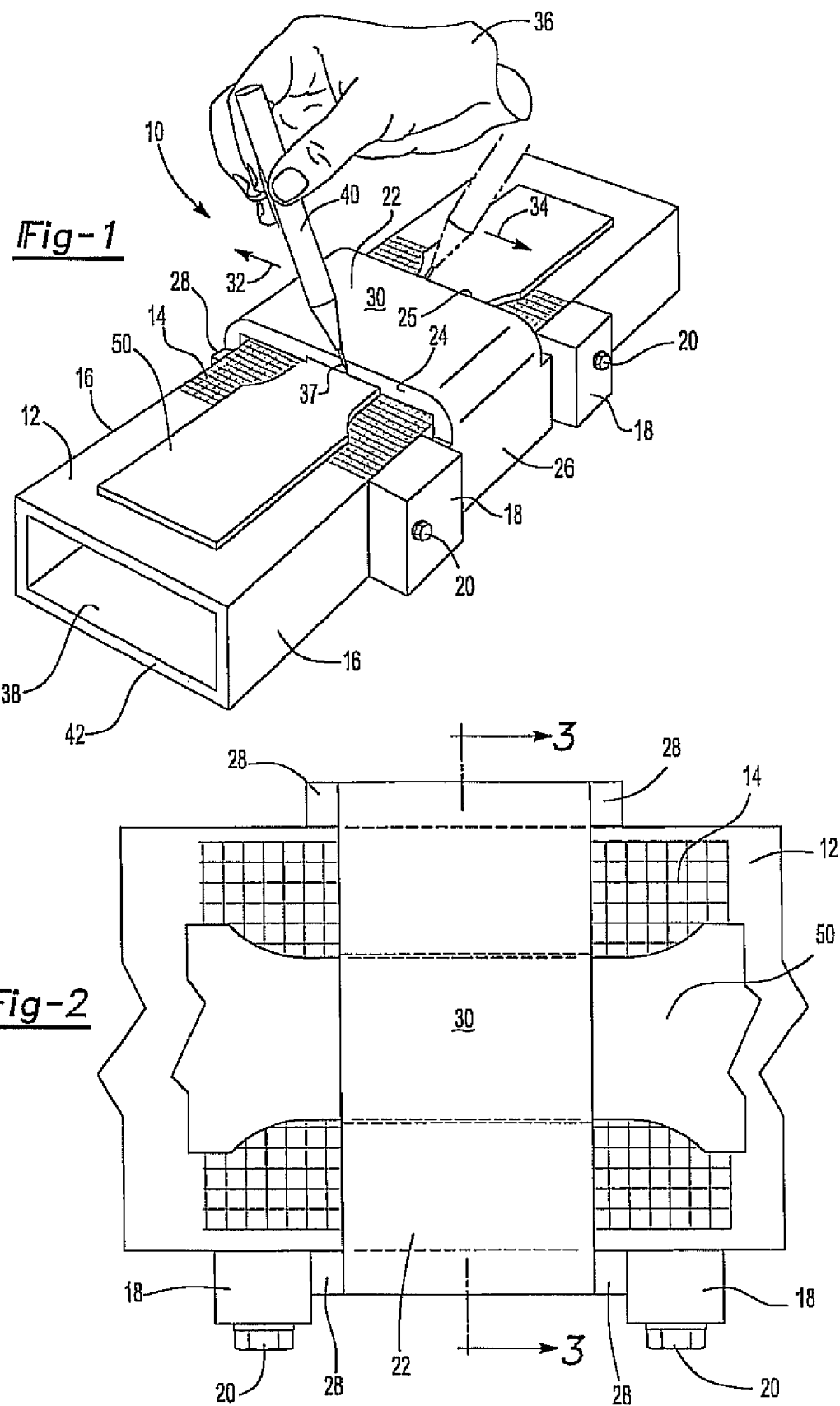

TENSILE BAR MARKING FIXTURE

FIELD OF THE INVENTION

This invention relates generally to an apparatus and method for marking test samples. Specifically, this invention relates to an apparatus and method for accurately scribing a tensile test sample bar with benchmarks before a tensile test is performed allowing for precise fit back measurement after testing to determine elongation.

BACKGROUND OF THE INVENTION

A tensile test, also known as a tension test, is a fundamental type of mechanical test performed on a material. Tensile tests are performed using a tensile test sample bar which is pulled at either end using a specified force for a predetermined amount of time, or until failure. A tensile test is performed to determine how a material will react to forces being applied in tension. Tensile strength, strain, yield strength, and the modulus of elasticity are all common factors measured during a tensile test.

To properly perform a tensile test, a tensile test sample bar is required to have accurate markings. These markings are measured before the tensile test takes place, during the tensile test, and after the tensile test. These measurements are used to calculate the various qualities of the material (i.e., modulus of elasticity). Benchmarks must be accurate to properly calculate these material properties. Benchmarks are used to allow fit back measurements to determine percent elongation upon fracture. The fractured sample, having fractured ends, is fit back together to determine the change in length between the benchmarks thereby determining the percent elongation. Traditionally, two lines, or benchmarks, are scribed into the tensile test sample bar by manually measuring the distance between the two scribed benchmarks. Manually measuring the space in between the benchmarks may result in an imprecise measurement thereby tarnishing post fracture measurements.

Furthermore, the process of manually measuring the spacing distance between the benchmarks is a time-consuming process.

Accordingly, it would be advantageous to provide an apparatus and method to more accurately and quickly measure and scribe benchmarks into a tensile test sample bar.

SUMMARY OF THE INVENTION

The present invention provides an apparatus and method to accurately scribe benchmarks into a tensile test sample bar. The apparatus includes a base having a planar surface allowing a tensile test sample bar to rest thereupon. The apparatus further includes a guide having two spaced apart edges separated by a predetermined width. The planar surface of the base further includes a plurality of grid lines to properly align the tensile test sample bar. The base further includes at least one securing member adapted to abut and secure the guide during scribing of the tensile test sample bar. The method includes the steps of aligning a tensile test sample bar on the planar surface having a plurality of grid lines and securing the tensile test sample bar on the planar surface by means of the securing members. The guide then provides for an accurate predetermined width of the spacing of the benchmarks scribed onto the tensile test sample bar. By means of a scribe, the user runs the scribe along each of the edges of the guide and scrapes two benchmarks onto the tensile test sample bar.

BRIEF DESCRIPTION OF THE DRAWINGS

The above and other features and objects of the invention will be better understood from the following detailed description of the typical embodiments illustrated in the accompanying drawings, in which:

FIG. 1 is a perspective view of the marking apparatus fully assembled holding a tensile test sample bar and a user scribing benchmarks onto the tensile test sample bar;

FIG. 2 is a top view of the fully assembled marking apparatus holding a tensile test sample bar;

DETAILED DESCRIPTION OF THE PREFERRED EMBODIMENTS

Figure 3:
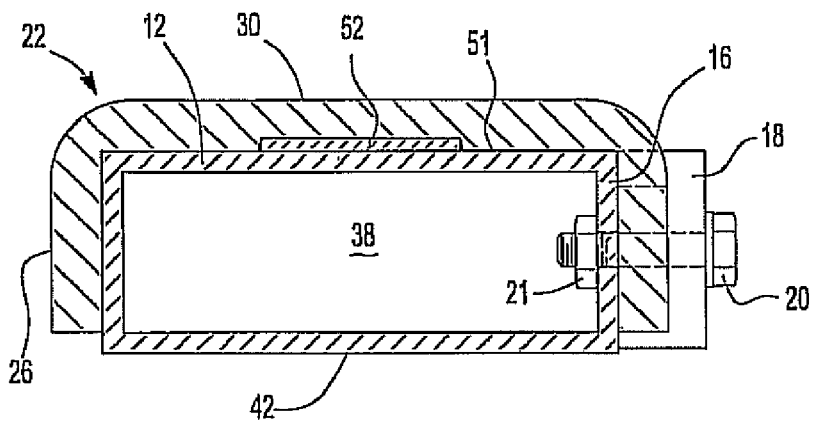
FIG. 3 is a cross section along the line 3-3 showing a fully assembled marking apparatus.

A tensile test sample bar marking apparatus and method are provided enabling accurate placement of benchmarks required to perform a tensile test. Now referring to FIGS. 1-5, the marking apparatus 10 includes a base 12 and a guide 30. The base 12 includes a planar surface optionally including a plurality of grid lines 14. Grid lines 14 are used to accurately position a tensile test sample bar 50.

The marking apparatus 10 further includes a guide 30 having two spaced apart edges 24, 25. The guide 30 may optionally include side members 26 enabling the guide 30 to wrap around the base 12 of the marking apparatus 10. In this embodiment, the base 12 includes two sidewalls 16 and a lower surface 42 thereby forming a rectangle-like box having an inner space 38. The marking apparatus 10 further includes at least one securing member 18 positioned on the sidewall 16. The securing members 18 are adapted to abut and secure the guide 30. The securing members 18 extend perpendicularly away from the sidewall 16. The securing members 18 may optionally include a bolt 20 to secure the securing member to the sidewall 16. In one embodiment, the securing members 18 are adjustable along the sidewall 16 of the marking apparatus 10.

The base 12 of the marking apparatus 10 may be comprised of a plurality of metals, such as aluminum, or any other strong and durable material. The guide 30 of the marking apparatus 10 is made from a strong material, preferably a metal such as steel. The securing members 18 are preferably made of a durable metal, such as aluminum.

The securing members 18 may be tightly secured to the sidewall 16 of the base 12 by means of a bolt 20. As shown in FIG. 3, the bolt 20 securing the securing member 18 to the sidewall 16 may further include a nut 21 to better secure the bolt 20.

In one embodiment, the guide 30 includes an indentation 52 within the lower surface 51 of the guide 30 adapted to accept the tensile test sample bar 50. More particularly, the indentation 52 is adapted to hold in place the tensile test sample bar at the midsection 53 of the tensile test sample bar 50.

Figure 4:
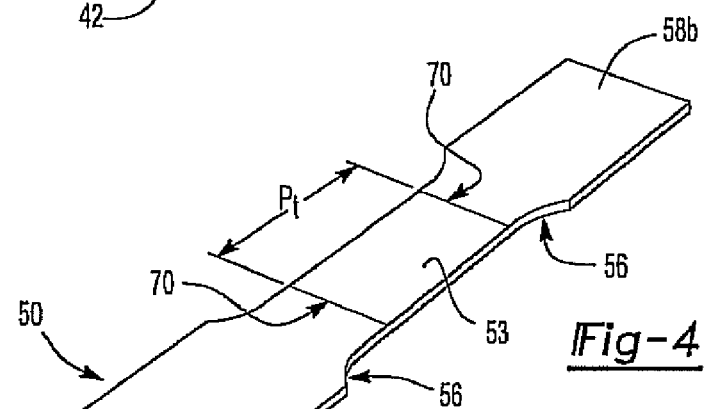
FIG. 4 is a perspective view of a tensile test sample bar.
Figure 5:
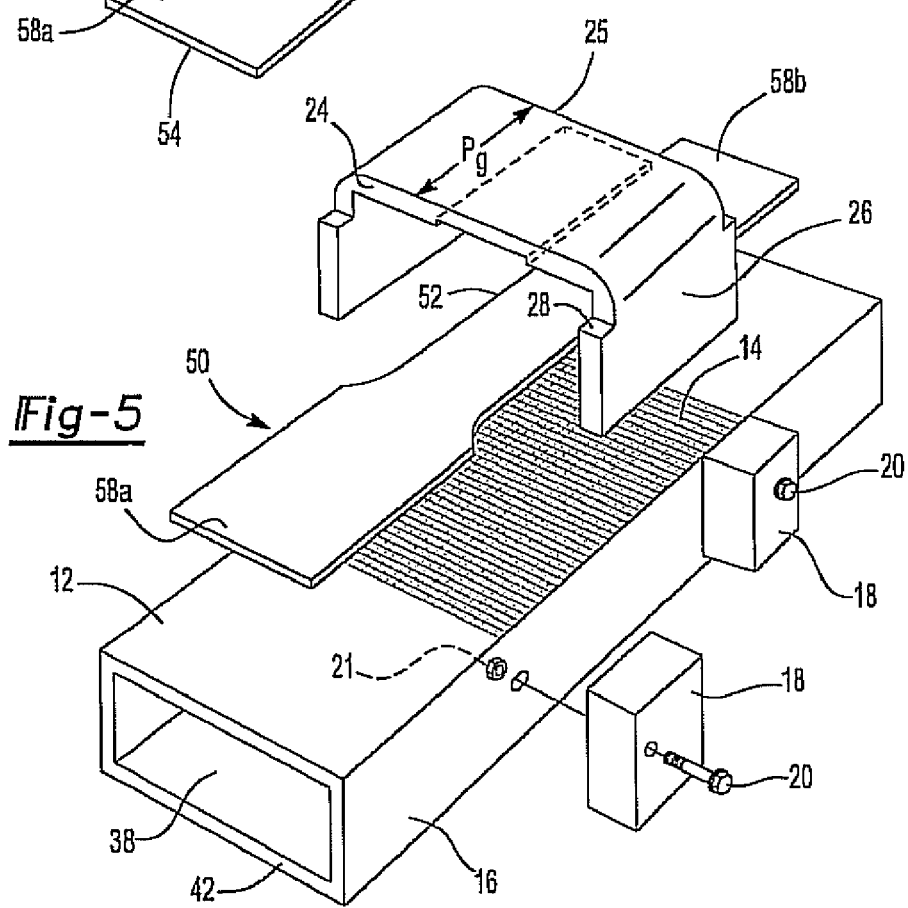
FIG. 5 is an exploded perspective view of the marking apparatus and the tensile test sample bar.

As shown by FIG. 4, the tensile test sample bar 50 includes a first end 58a and a second end 58b. During a tensile test, the tensile test sample bar 50 is pulled at the first end 58a and the second end 58b. The tensile test sample bar 50 includes a midsection 53 wherein the width of the midsection 53 is less than that of the width of the tensile test sample bar 50 at the first end 58a and the second end 58b. The first end 58a transitions to the midsection 53 by means of a radiused edge 56 which tapers the first end 58a to the midsection 53. Similarly, the second end 58b tapers to the midsection 53 by means of the radiused edge 56.

The tensile test sample bar 50 further includes two benchmarks 70 spaced apart by a predetermined width $P_t$. Predetermined width $P_t$ ranges between 30 and 70 millimeters, averaging at 50 millimeters. Typically, the benchmarks 70 have a predetermined width $P_t$ of 50 millimeters.

Figure 6:
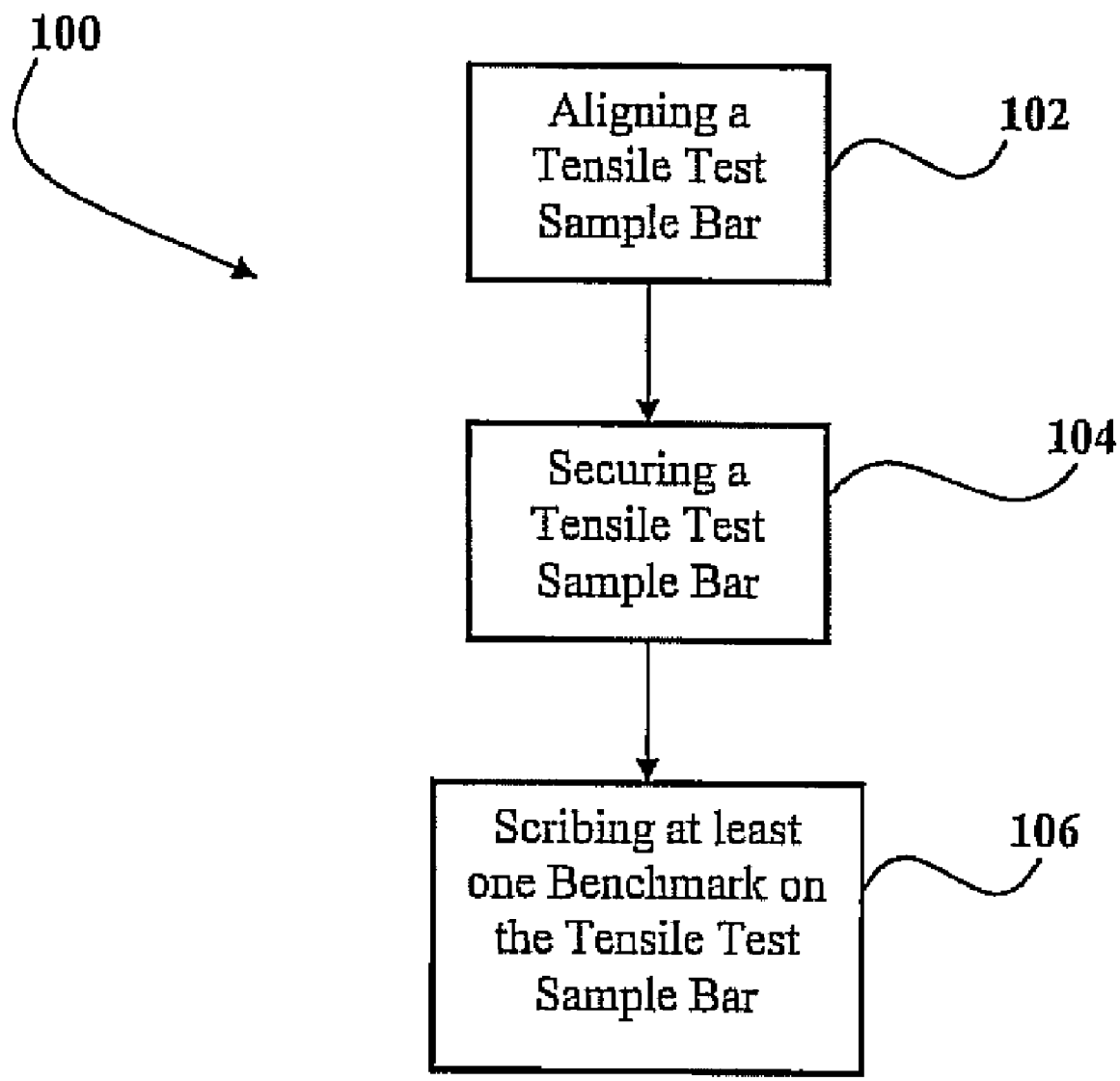
FIG. 6 is a schematic representation of the method as disclosed in the present invention.

Referring now to FIG. 6, a method 100 of accurately scribing 106 the tensile test sample bar 50 using the marking apparatus 10 comprises the steps of aligning 102 the tensile test sample bar 50 using the grid lines 14 on the planar surface of the base 12. The tensile test sample bar 50 is then secured 104. The guide 30 is placed over the tensile test sample bar 50 wherein the indentation 52 of the guide 30 securely rests over the midsection 53 of the tensile test sample bar 50. The securing members 18 abut and secure the guide 30. After the tensile test sample bar is secured 104, a user 36 scribes 106 a tensile test sample bar 50. The user 36 uses the scribe 40 to create etchings, also known as benchmarks 70, into the tensile test sample bar 50.

The guide 30 precisely spaces the benchmarks 70 according to the predetermined width $P_t$. Scribe 40 includes a sharp point 37 adapted to etch the metal of the tensile test sample bar 50. Once the tensile test sample bar 50 is securely in place under the guide 30, the user 36 scribes two benchmarks 70 into the tensile test sample bar 50. The user 36 creates the benchmarks 70 by closely abutting the spaced apart edges 24, 25 of the guide 30 during the etching process.

It is also to be understood that, although the foregoing description and drawings describe and illustrate in detail working embodiments of the present invention, to those skilled in the art to which the present invention relates, the present disclosure will suggest many modifications and embodiments. The present invention, therefore, is intended to be limited only by the scope of the appended claims and the applicable prior art.

We claim:

1. A marking apparatus adapted to facilitate benchmarking of a tensile test sample bar before tensile testing, the marking apparatus comprising:
    a base having a planar surface; and
    a guide having two spaced apart edges, the guide further having at least one end portion, the guide having at least one securing member operable to hold the at least one end portion and secure the guide, the spaced apart edges separated by a predetermined width thereby allowing for predetermined spacing of benchmarks on the tensile test sample bar.

2. The apparatus of claim 1, wherein the planar surface of the base includes a plurality of grid lines.

3. The apparatus of claim 1, wherein the base further includes at least one sidewall.

4. The apparatus of claim 3, wherein the at least one sidewall of the base further includes at least one securing member adapted to abut and secure the guide, the at least one securing member extending perpendicularly away from the at least one sidewall.

5. The apparatus of claim 4, wherein the at least one securing member of the base is adjustable.

6. The apparatus of claim 1, wherein the marking platform is aluminum.

7. The apparatus of claim 1, wherein the spaced apart edges of the guide are generally perpendicular to the planar surface of the base.

8. The apparatus of claim 1, wherein the guide further includes an upper surface and a lower surface.

9. The apparatus of claim 8, wherein the lower surface of the guide includes a recess allowing the tensile test sample bar to rest therein thereby preventing movement of the tensile test sample bar.

10. The apparatus of claim 1, wherein the predetermined width of the guide is between 30-70 millimeters.

11. A method of accurately marking a tensile test sample bar comprising the steps of:
    aligning a tensile test sample bar on a planar surface having a plurality of grid lines;
    securing the tensile test sample bar on the planar surface by securing a guide having two spaced apart edges over and around the tensile test sample bar;
    scribing at least one benchmark on the tensile test sample bar by scraping a sharp tool on the tensile test sample bar along the at least one edge of the guide.

12. The method of claim 11, wherein the two spaced apart edges of the guide are spaced apart in accordance to a predetermined width.

13. The method of claim 12, wherein the predetermined width of the guide is between 30-70 millimeters.

14. A marking apparatus adapted to facilitate benchmarking of a tensile test sample bar before tensile testing, the marking apparatus comprising:
    a base having a planar surface; and
    a guide having two spaced apart edges, the guide having a lower surface, the lower surface of the guide having a recess allowing the tensile test sample bar to rest therein thereby preventing movement of the tensile test sample bar, the spaced apart edges separated by a predetermined width thereby allowing for predetermined spacing of benchmarks on the tensile test sample bar.

* * * * *